US009931240B2

(12) United States Patent
Wilford et al.

(10) Patent No.: US 9,931,240 B2
(45) Date of Patent: Apr. 3, 2018

(54) THERAPEUTIC WRAP

(71) Applicants: Michael L Wilford, Chicago, IL (US); David Slack, Carmel, IN (US)

(72) Inventors: Michael L Wilford, Chicago, IL (US); David Slack, Carmel, IN (US)

(*) Notice: Subject to any disclaimer, the term of this patent is extended or adjusted under 35 U.S.C. 154(b) by 488 days.

(21) Appl. No.: 14/730,470

(22) Filed: Jun. 4, 2015

(65) Prior Publication Data

US 2015/0297440 A1    Oct. 22, 2015

Related U.S. Application Data

(62) Division of application No. 13/543,936, filed on Jul. 9, 2012, now Pat. No. 9,132,057.

(51) Int. Cl.
| | | |
|---|---|---|
| *A61H 9/00* | (2006.01) | |
| *A61F 7/02* | (2006.01) | |
| *A61H 1/00* | (2006.01) | |
| *A61F 7/00* | (2006.01) | |

(52) U.S. Cl.
CPC ............. *A61F 7/02* (2013.01); *A61H 1/008* (2013.01); *A61H 9/005* (2013.01); *A61H 9/0078* (2013.01); *A61H 9/0092* (2013.01); *A61F 2007/003* (2013.01); *A61F 2007/0024* (2013.01); *A61F 2007/0027* (2013.01); *A61F 2007/0039* (2013.01); *A61F 2007/0046* (2013.01); *A61F 2007/0056* (2013.01); *A61F 2007/0228* (2013.01); *A61F 2007/0257* (2013.01); *A61F 2007/0271* (2013.01); *A61F 2007/0295* (2013.01); *A61H 2201/0207* (2013.01); *A61H 2201/0214* (2013.01); *A61H 2201/164* (2013.01); *A61H 2201/165* (2013.01);

(Continued)

(58) Field of Classification Search
CPC .... A61H 9/005; A61H 9/0078; A61H 9/0085; A61H 9/0092; A61H 2201/0103; A61H 2205/062; A61H 2209/00; A61H 2201/1614; A61H 2201/1616; A61H 2201/1645; A61H 2201/1647; A61H 2201/165; A61F 5/39; A61F 5/012
See application file for complete search history.

(56) References Cited

U.S. PATENT DOCUMENTS

| | | |
|---|---|---|
| 4,225,989 A | 10/1980 | Corbett et al. |
| 5,169,384 A | 12/1992 | Bosniak et al. |
| 5,437,610 A | 8/1995 | Cariapa et al. |

(Continued)

OTHER PUBLICATIONS

Author: Thermotek, Inc.; Title of Item: FDA Section 510(k) submission, Releasable Version Date: May, 3, 2010; See attached for additional information.

*Primary Examiner* — Michael Tsai
(74) *Attorney, Agent, or Firm* — Olson & Cepuritis, Ltd.

(57) ABSTRACT

The subject matter of the invention relates to therapy wraps for the application of compression and/or thermal therapy to a patient. The wraps are formed of at least two layers of material which are sealed together to form at least one cavity between them. The wraps may be used in conjunction with a therapy machine which fills the cavity or cavities of the wraps with fluid such as a gas and/or a liquid. The unique shapes of the wraps are particularly suitable for providing therapy to the human body. The shapes permit the manipulation of the wraps around various portions of the human body such as the shoulder, back and foot.

11 Claims, 8 Drawing Sheets

(52) U.S. Cl.
CPC ............. *A61H 2201/1614* (2013.01); *A61H 2201/1619* (2013.01); *A61H 2201/1635* (2013.01)

(56) References Cited

U.S. PATENT DOCUMENTS

| | | |
|---|---|---|
| 5,466,250 A | 11/1995 | Johnson, Jr. et al. |
| 5,584,798 A | 12/1996 | Fox |
| 5,733,321 A | 3/1998 | Brink |
| 5,865,841 A | 2/1999 | Kolen et al. |
| 5,894,615 A | 4/1999 | Alexander |
| 5,925,010 A | 7/1999 | Caprio, Jr. |
| 5,989,285 A | 11/1999 | DeVilbiss et al. |
| 6,080,120 A | 6/2000 | Sandman et al. |
| 6,290,662 B1 | 9/2001 | Morris |
| 6,352,550 B1 | 3/2002 | Gildersleeve |
| 6,440,093 B1 | 8/2002 | McEwen et al. |
| 6,530,941 B1 | 3/2003 | Muller et al. |
| 6,551,347 B1 | 4/2003 | Elkins |
| 6,610,084 B1 | 8/2003 | Torres |
| 6,736,787 B1 | 5/2004 | McEwen et al. |
| 7,198,093 B1 | 4/2007 | Elkins |
| 7,207,959 B1 | 4/2007 | Chandran |
| 7,211,104 B2 | 5/2007 | Edelman |
| 7,354,410 B2 | 4/2008 | Perry et al. |
| 7,396,345 B2 | 7/2008 | Knighton et al. |
| 7,442,175 B2 | 10/2008 | Meyer |
| 7,896,910 B2 | 3/2011 | Schirrmacher et al. |
| 2004/0039317 A1* | 2/2004 | Souney ............ A61H 9/0078 602/13 |
| 2005/0070828 A1 | 3/2005 | Hampson et al. |
| 2005/0143797 A1 | 6/2005 | Parish et al. |
| 2008/0058911 A1 | 3/2008 | Parish et al. |
| 2008/0195012 A1* | 8/2008 | Miros ............... A61F 5/0106 602/26 |
| 2009/0069731 A1 | 3/2009 | Parish et al. |
| 2010/0210982 A1 | 9/2010 | Balachandran et al. |
| 2012/0172774 A1 | 7/2012 | Lowe et al. |

* cited by examiner

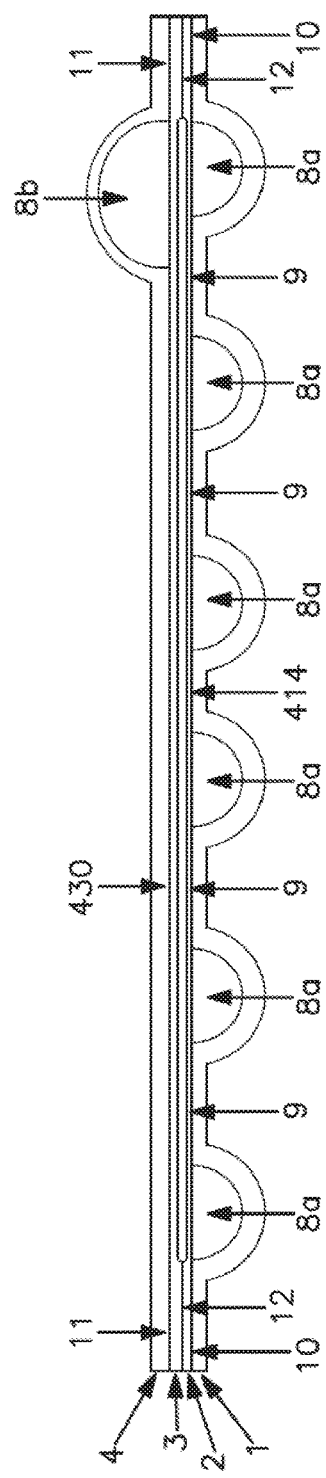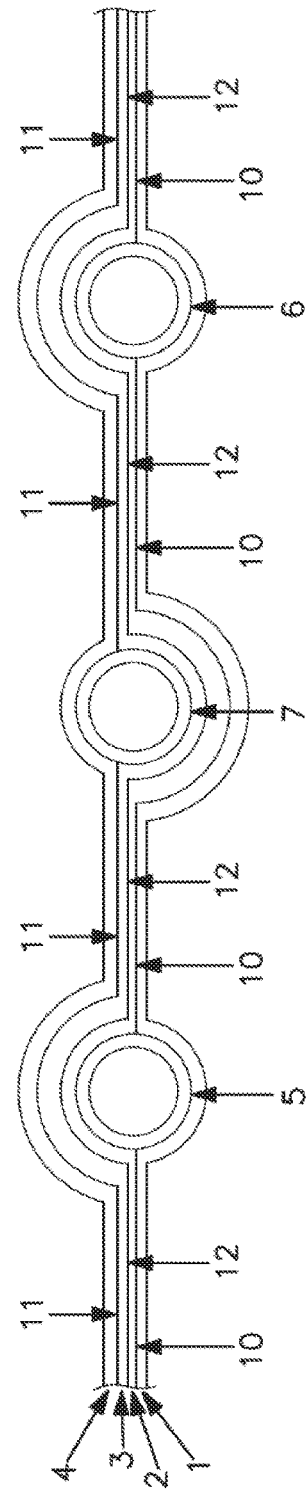

THERAPEUTIC WRAP

CROSS-REFERENCE TO RELATED APPLICATION

This application is a divisional application of, and claims priority to, U.S. patent application Ser. No. 13/543,936 filed Jul. 9, 2012 on behalf of Wilford, et al., the entirety of which is incorporated herein by this reference.

FEDERALLY SPONSORED RESEARCH OR DEVELOPMENT

Not Applicable.

BACKGROUND OF THE INVENTION

The present invention relates generally to thermal and compression systems used in the application of thermal and compression therapy to a patient's body. More particularly, the invention is directed to removable wraps that are applied to a portion of the patient's body, for example, a patient's back, shoulder or foot. The wraps include at least one fluid-tight chamber allowing for the ingress and egress of a fluid. The ingress of a fluid, which may also be heated or cooled, into the fluid-tight chamber applies compression and/or thermal therapy to the patient's body in the location of the wrap.

Compression and thermal wraps similar to the invention described herein have been in use for many years. The wraps are designed to be applied an area of the patient's body where therapy is desired. Once in place, a fluid (either a gas or a liquid) is forced into a fluid-tight chamber of the wrap thereby applying therapy to the portion of the patient's body contacted by the wrap. Such wraps are often used in the treatment and prevention of deep vein thrombosis, but may have other uses as well.

Prior wraps were constructed of two or more layers of material, sealed together to form a fluid tight chamber. The fluid-tight chamber, or fluid-tight chambers of such wraps could then be subdivided into smaller fluid-tight chambers, or could have one or more pathways formed within them. Such wraps have been made into a variety of shapes. Examples of different wraps are described in U.S. Pat. No. 7,198,093 issued to Elkins, U.S. Pat. No. 7,211,104 issued to Edelman, U.S. Pat. No. 5,466,250 issued to Johnson, Jr. et al., U.S. Pat. No. 7,442,175 issued to Meyer et al., U.S. Pat. No. 6,352,550 issued to Gildersleeve et al., U.S. Pat. No. 5,411,541 issued to Bell et al., and U.S. Patent Application Publication 2008/0058911 filed on behalf of Parish et al.

Wraps of the aforementioned construction suffer from a number of shortcomings. Particularly, the shape of each wrap identified, as well as others in the prior art fail to adequately conform to the human body. To achieve optimal therapy, the wrap must be secured to that portion of the body where therapy is desired and remain in place throughout the therapy session. That is particularly difficult when therapy is desired on an irregularly shaped portion of the body such as, for example, a shoulder. Consequently, the therapeutic wraps associated with the present invention solve the problems plaguing prior wraps by uniquely shaping wraps to provide optimal therapy to the body.

As described in detail below, the present invention provides a unique solution to the aforementioned problems.

SUMMARY OF THE INVENTION

The present invention relates to uniquely shaped therapy wraps. The wraps may be constructed of two or more layers of material which are sealed together to from a fluid tight cavity bounded by a cavity seal. Additionally, at least one hose is provided such that one end of the hose is in fluid communication with the interior of the cavity while the other end of the hose is in fluid communication with the environment. The hose may be provided with various valves to assist in the control of fluid moving from the environment into and/or out of the interior of the cavity.

Three particularly shaped wraps are provided. The first wrap is preferably in the shape of a rectangle or a capital letter H having a small flap on one lower portion of the wrap and an elongated arm on the other lower portion. The hose or hoses are positioned at the end of the elongated arm such that fluid is forced into the elongated arm first and then permitted to travel into the main body of the wrap. Preferably, the wrap is utilized to provide therapy to a person's lower back. The main body portion of the wrap is laid across the persons lower back such that the elongated arm is allowed to curve around the person's torso. Having the hoses attached to the elongated arm prevents the hoses from being kinked or blocked by a person's body weight when the person is seated or supine. It also alleviates the discomfort that would otherwise be experienced by the person if they were resting against the hoses while therapy was being applied. Furthermore, the placement of the hoses provides easy access to the ends of the hoses open to the environment because the elongated arm wraps around the torso so as to be at the side or in front of the person utilizing the wrap. With the hoses and arm located thusly, the person can easily monitor the ingress an egress of fluid to and from the wrap by testing or feeling the elongated arm.

The second wrap is generally in the shape of a capital letter T or Y. It has three lobes, one of which is equipped with one or more hoses. That wrap is preferably utilized to provide therapy to a persons shoulder. In use, the first two lobes, without the hoses, may be connected together in front of or behind the third flap having the hoses. Bringing the two lobes together in that manner alters the three-dimensional shape of the wrap, transforming it from an essentially flat wrap into a cup shape. The cup may then be placed over the persons shoulder and the three lobes will rest against and encompasses the shoulder muscles. Preferably, the wrap is further held in place by an elastic strap which is wrapped around the person's torso and connected to the exterior of the wrap. Placing the hoses in the third lobe allows the hoses to comfortably hang down along the persons arm regardless of the size of the individual. That is, the orientation of the first two lobes may be easily altered to accommodate both large and small individuals, but the orientation of the hoses will remain essentially constant, hanging down along the arm.

The third wrap is generally in the shape of a trapezoid connected to a pentagon. That is, the top of the wrap is generally in the shape of a pentagon, having a top that is shorter in length than the base. The base is connected to a lower portion of the wrap which is generally in the shape of a pentagon. The point of the pentagon is connected to the base of the trapezoid to form the entire wrap. Furthermore, one or more hoses are provided, entering the cavity of the wrap along the base of the pentagon, that is, the side of the pentagon opposite of the connecting point. Preferably the wrap is utilized to provide therapy to a person's foot and ankle. The wrap may be applied by placing a person's foot on the wrap such that the person's heal is located in the trapezoid, the arch of the foot crosses the connection point between the trapezoid and the pentagon, and the toes of the person are located in the pentagon. The wrap is then manipulates so as to wrap around the persons ankle and/or lower calf as well as around the top of the person's foot and toes. Having the hoses positioned along the base of the pentagon ensures that fluid entering the cavity of the third wrap moves from the person's toes, back along the foot toward the ankle, then up the ankle to the lower calf. By directing fluid in such a manner, it is possible to create a pressure gradient that moves along the person's foot and pushed bodily fluid, such as blood, away from the toes and back into the person's leg.

The wraps constructed according to the present invention may be used to apply compression and thermal therapy to a body. It is contemplated that the wraps could be used to apply such therapy by using the wraps in conjunction with a compression and thermal therapy machine such as the device disclosed in U.S. Patent Application Publication No. U.S. 2001/0257565. That device is equipped with a number of ports which may be connected to the hose or hoses of the wraps discussed herein. The device provides fluid in the form of a thermal liquid or gas through the hoses connected to the ports and into the wraps in order to provide thermal and or compression therapy.

BRIEF DESCRIPTION OF THE DRAWINGS

FIG. 4A is an exemplary cross-sectional view of cross-section A referenced in FIG. 4 depicting layers of material, seals, and cavities forming the therapy wraps.

FIG. 5A is an exemplary cross-sectional view of cross-section B referenced in FIG. 5 depicting layers of material, seals, and hoses forming the therapy wraps with the hoses traversing the seals that surround the therapy wraps.

DETAILED DESCRIPTION OF THE PREFERRED EMBODIMENTS

Figure 1:
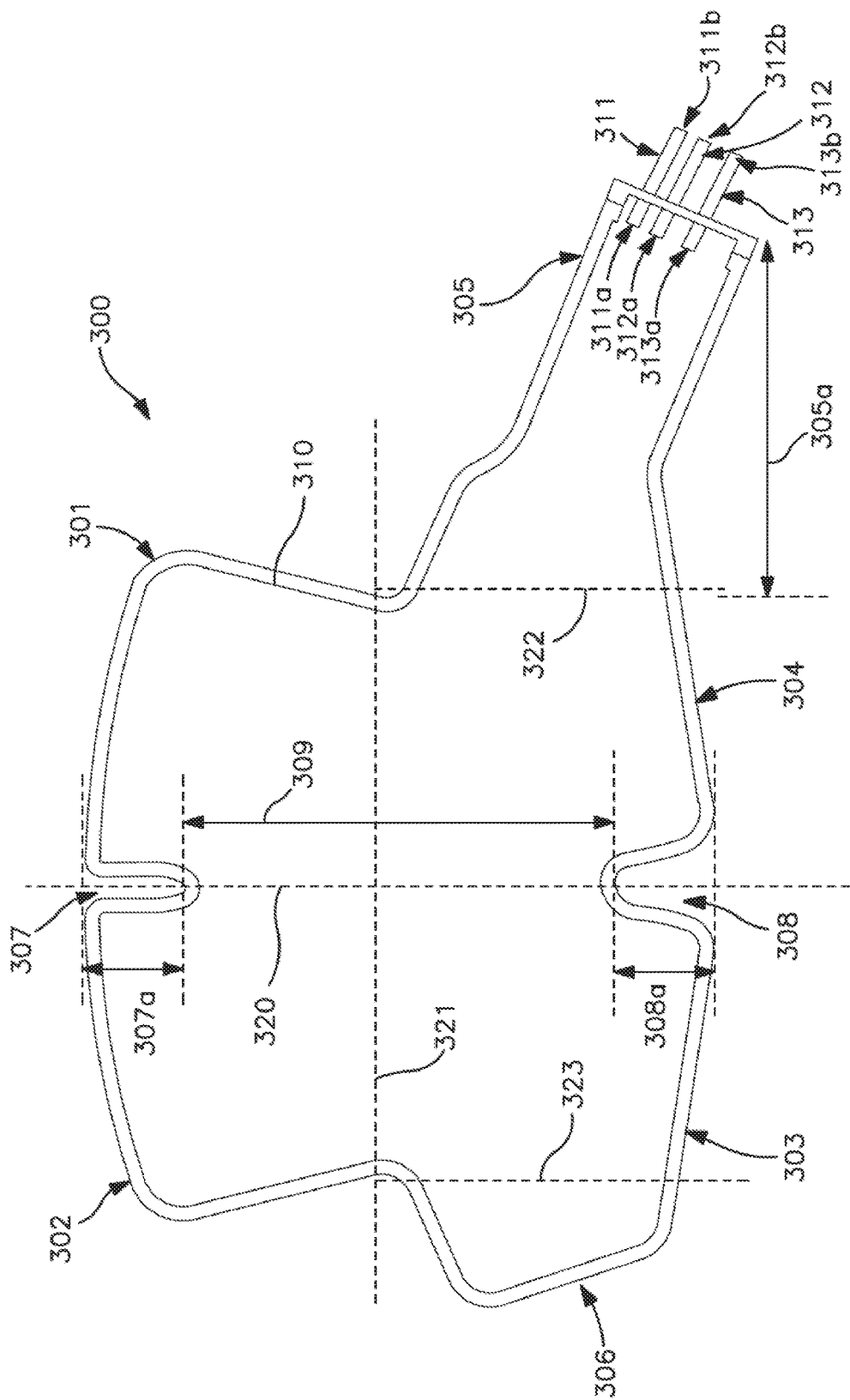
FIG. 1 is a plan view of a wrap having an elongated arm.

Throughout the specification, wherever practicable, like structures will be identified by like reference numbers.

It is preferable that the therapy system of the present invention is used to apply thermal and/or compression therapy utilizing various specially designed wraps. The particular shape and benefits afforded by the various specially designed wraps for use with the therapy system will be described in detail below. The wraps may be constructed for the application of thermal treatment using a circulated heated or cooled fluid, the application of compression therapy, or both. Thermal therapy only wraps may be constructed utilizing at least two layers of material and at least two hoses. The two or more layers of material and two or more hoses are laminated together at least about the perimeter of the two layers of material thereby forming a cavity between at least two or more layers and such that the two hoses provide pathways for the ingress and egress of fluid to and from the cavity. Alternately, the wrap designs could be utilized for compression therapy utilizing two or more layers of material and at least one hose. In such an embodiment the two or more layers of material and the at least one hose are sealed together about the perimeters of the material thereby forming a cavity between them with the one or more hoses providing a pathway for the ingress and egress of fluid, preferably compressed gas, to the cavity. In the preferred embodiments, the basic construction of each is essentially the same. Each wrap includes at least three, but preferably four, fluid tight layers of material and at least three hoses. The three or more layers of material and at least three hoses are sealed together, for example using radio frequency (RF) welding, so as to create at least two fluid tight chambers between them, such that fluid is permitted ingress to and egress from the chambers by way of the hoses. Material suitable for constructing wraps include 200 Denier nylon oxford laminated to polyurethane for use in creating the exterior layers, with interior layers being made of polyurethane alone. Such material may be purchased from a variety of companies including Lamcotec of 152 Bethany Road, PO Box 279, Monson, Mass. 01057.

It should be understood that the hose and/or hoses referred to herein are in the simplest sense a pieces of conduit that provide an access pathway from the exterior of a fluid tight cavity to the interior of the fluid tight cavity. The hose may be of more complex design however, such as a multiple pieces of conduit having one or more valves or connection pieces all coupled together which essentially provide the same pathway between the exterior and interior of the fluid tight cavity. Preferably, the hose is simply a hose which provides the pathway between the interior of the cavity and the exterior of the fluid tight cavity by traversing the seal between the layers of material which define the fluid tight cavity. However, the hose could alternatively be a port which is formed in the sidewall of the fluid tight cavity to which another hose may be connected.

The preferred construction of each of the wraps recited below with reference to FIGS. 4A and 5A which are each exemplary cross-sectional views, taken along cross-sectional lines A and B, respectively, of the embodiment of the shown in FIGS. 4-5. A first sheet 1 of polyurethane is provided having one side coated with nylon. The nylon side is placed face down such that the polyurethane side is facing up. Two hoses 5, 6 are place on top of the first sheet such that the hoses each cross over the perimeter of the first sheet and thus a first end of a first hose and a first end of a second hose each rest on top of the first sheet. The second end of the first hose and the second end of the second hose are each oriented such that each is in contact with the open air. Preferably, the hoses are oriented such that the longitudinal axis of each hose aligns perpendicularly to the perimeter of the first sheet at the point at which each hose crosses the perimeter of the first sheet. A second sheet 2 of polyurethane material of substantially the same size and shape as the first sheet 1 is oriented over the first sheet 1 and laid on top of the first sheet 1 such that the perimeters of both the first and second sheets substantially line up. The second sheet 2 thus substantially covers the first sheet and covers the first end of the first hose and the first end of the second hose. A third sheet 3 of polyurethane substantially the same size and shape as the first and second sheets 1, 2 is laid on top of the second sheet 2. A third hose 7 is laid on top of the third sheet 3 such that it crosses over the perimeter of the third sheet and thus a first end of the third hose rests on top of the third sheet. The second end of the third hose is oriented such that it is in contact with the open air. As with the first and second hoses 5, 6, it is preferred that the third hose 7 is oriented such that the longitudinal axis of the third hose aligns perpendicularly to the perimeter of the third sheet at the point at which the third hose crosses the perimeter of the third sheet. A fourth sheet 4 of polyurethane coated with nylon, having substantially the same size and shape as the first, second and third sheets, is laid on top of the third sheet 3 such that the perimeters of all four sheets substantially align; the fourth sheet covers the first end of the third hose and is laid on top of the other sheets such that the nylon coating is facing away from the third sheet.

The four sheets may then be sealed together, preferably about their perimeters. The seal is formed such that the first and second sheets 1, 2 are sealed 10 together thereby creating a first cavity 8a between the first and second sheet 1, 2 where the first and second hoses 5, 6 are sealed between the first and second sheets such that first end of the first hose and the first end of the second hose communicate with the cavity between the first and second sheets. Because the first end of the first hose and the first end of the second hose communicate with the first cavity and the second end of the first hose and the second end of the second hose communicate with the open air, fluid may be passed through the first or second hose to either fill or drain the first cavity. Similarly, the third sheet 3 and fourth sheet 4 are sealed 11 together, preferably about their perimeters, thereby creating a second cavity 8b between the third sheet and fourth sheet where the third hose 7 is sealed between the third sheet and fourth sheet such that the first end of the third hose is in communication with the second cavity 8b between the third sheet and fourth sheet. Because the first end of the third hose is in communication with the second cavity and the second end of the third hose is in communication with the open air, fluid may be passed through the third hose 7 to either fill or drain the second cavity. The first, second, third and fourth sheets are also all sealed 12 together, preferably about their perimeter, thereby creating one wrap having at least two cavities and two or more hoses such that a first cavity includes at least one hose in communication with the interior of the first cavity and a second cavity includes at least one hose in communication with the second cavity. It should be appreciated that the seals sealing together the first and second sheets and sealing together the third and fourth sheets form continuous paths encircling the entirety of the cavities formed between the first and second sheet and between the third and fourth sheet, respectively. The seal forming the first cavity further surrounds the exterior of the first and second hoses 5, 6, while the seal forming the second cavity surrounds the exterior of the third hose 7 such that the only avenue for fluid to ingress to and egress from the first cavity 8a is through the first or second hoses 5, 6 and the only avenue for fluid to ingress to and egress from the second cavity 8b is through the third hose 7. Additional pattern seals 9 may also be formed. The wraps may also include fasteners, such as hook and loop, snaps, buttons, eyelets or other type of fasteners.

It should be apparent that additional hoses could be sealed between either the first and second layers or between the third and fourth layers or even between any number of additional layers. It should also be apparent that while it is preferable that the at least four layers of material are sealed together such that only one seal is necessary to form the first cavity, second cavity and connect the layers of material together, multiple seals could be utilized. That is, a first cavity seal could be used to seal together a first layer and a second layer to form a first cavity, a second cavity seal could be used to seal together a third layer and a fourth layer to form a second cavity and a third connecting seal could be used to seal at least one of the first or second layers of material to at least one of the third or fourth layers of material. The first cavity seal, second cavity seal, and connecting seal could each be of unique size and shape such that when the four layers of material are connected together along the connecting seal, none of the three seals overlap. Alternately, the three seals could partially overlap when the layers of material are connected together. Alternately, and preferably, all three seals, the first cavity seal, second cavity seal and connecting seal are all formed at the same time such that they are essentially one in the same seal, entirely overlapping and congruous with one another.

Bearing in mind the aforementioned general construction of the wraps, a number of specially designed wraps will now be described with reference to FIGS. 1 trough 7. In FIG. 1, a wrap 300 is provided. Wrap 300 is constructed as described above such that at least one hose, a first sheet and a second sheet are sealed about the perimeter of the sheets thereby forming a first cavity having a hose for fluid transfer, at least one additional hose, a third sheet and a fourth sheet are sealed together about the perimeter of the sheets thereby forming a second cavity having a hose for fluid transfer, and all four of the sheets are sealed together to form the overall wrap. The wrap according to FIG. 1 has five general portions (roughly delineated by hash lines 321, 322, and 323) a first lobe 301, a second lobe 302, a third lobe 303, a fourth lobe 304 and an elongated arm 305. In the embodiment depicted in FIG. 1, lobe 303 of wrap 300 also includes a flap 306. Flap 306 extends lobe 303 to so that the wrap may partially curve around an individual's lower torso during the application of therapy to a person's lower back.

The four lobes, 301, 302, 303, and 304 make up the primary body portion of the wrap, which essentially forms the shape of a rectangle or capital letter H. As shown in FIG. 1, the primary body portion is of greater surface area than the elongated arm. While the four lobes, flap 306 and the elongated 305 may be said to be connected, it should be appreciated that they are not necessarily brought together as separate pieces and sealed together but instead, and preferably, are constructed from a uniform sheets of material with the connection points simply being imaginary lines 320, 321, 322 and 323. The same may be said of the connection between lobes of the wraps discussed with respect to any of FIGS. 1-7.

As shown in FIG. 1, lobes 301 and 302 come together at an indentation point 307 and lobes 303 and 304 come together at indentation point 308. Indentation points 307 and 308 are substantially shaped like the capital letters U or V. The depth indentation 307, that is, the distance between the top of lobes 301 and 302 and the bottom well of indentation point 307, is identified as 307a. The depth of indentation 308, that is, the distance between the top of lobes 303 and 304 and the bottom well of indentation point 308, is identified as 308a. The distance between indentation point 307 and indentation point 308 is identified as 309. It is preferred that 307a and 308a are substantially the same if not equal. Additionally, it is preferred that the length 309 is greater than either 307a or 308a.

Surrounding the perimeter of wrap 300 is seal 310. Seal 310 forms a first cavity between the first and second sheets of material and a second cavity between the third and fourth sheets of material. As shown in FIG. 1, arm 305 extends from lobe 304 and has a length 305a. Also as shown in FIG. 1, wrap 300 includes three hoses, 311, 312 and 313. The three hoses are provided at the distal end of arm 305. Preferably, the hoses cross the perimeter of the wrap 300 at the distal end of arm 305, the seal 310 being formed around the exterior of each hose so as not to block the interior passageway of any hose.

Each hose has two ends, a first end and a second end. The first ends of hoses 311 and 313 are identified as 311*a* and 313*a*, respectively. 311*a* and 313*a* communicate with the first cavity. The second ends of hoses 311 and 313 are identified as 311*b* and 313*b*, respectively. Hose ends 311*b* and 313*b* communicate with the open air. The first end of hose 312 is identified as 312*a* and it communicates with the second cavity. The second end of hose 312 is identified as 312*b* and it communicates with open air. Thus, fluid may only ingress to and egress from the first cavity by way of hoses 311 and 313, and fluid may only ingress to and egress from the second cavity by way of hose 312. While the hoses 311, 312 and 313 may be of any length, it is preferred that the portion of each hose that communicates with cavities one or two does not extend the entire length arm 305. Preferably, length 305*a* of arm 305 is between 15-30 centimeters and the lengths of those portions of hoses 311, 312 and 313 which communicate with cavities one or two, that is, the portions of hoses 311, 312 and 313 extending from seal 310 into wrap 300, are approximately 1 centimeter or less each.

The shape of wrap 300 is dictated by the area of the body it is designed to apply therapy to, namely the lower back. In use, wrap 300 is designed to be placed on an individual's lower back such that length 309 is placed over the individual's spinal column. In such an orientation, lobe 301 may provide therapy to the individual's right latissimus dorsi area, lobe 302 may provide therapy to the individual's left latissimus dorisi area while lobes 303 and 304, resting on or above the individual's left and right gluteus maximus, respectively, may apply therapy to the individual's lower back. Arm 305, extending as it does from lobe 304, wraps further around the individual's torso, providing easy access to the hoses 311, 312, 313 generally in the area of the individual's right front hip. Orienting the hoses at the distal end of arm 305 ensures that the flow of fluid is not inhibited at 311*a*, 312*a* or 313*a* as a result of the individual's bodyweight resting on the wrap when sitting or supine. The location of the hoses on arm 305 also eliminates the discomfort of resting on top of the hoses when seated or supine and allows the person to easily monitor the flow of fluid.

When wrap 300 is not in use, its profile is substantially flat, being defined only by the thickness of the four sheets of material from which it is made and the hoses. However, when in use, the profile of wrap 300 grows and changes due to the ingress of fluid. As fluid ingresses into cavities one, two, or both, the thickness of wrap 300 increases, and the wrap begins to deform and thicken. When the wrap is applied to an individual, the wrap must curve around the individual's torso and curve along the spine as well. The indentations 307 and 308 provide flex points for the wrap such that when the wrap begins to deform and thicken, the lobes 301, 302, 303 and 304 flex at 307 and 308, allowing a greater surface area of the back to be contacted by the wrap than would be possible were the wrap strictly square or rectangular. Thus, Indentations 307 and 308 help ensure that the wrap stays flush against the therapy area and does not kink or bunch during therapy.

Figure 2:
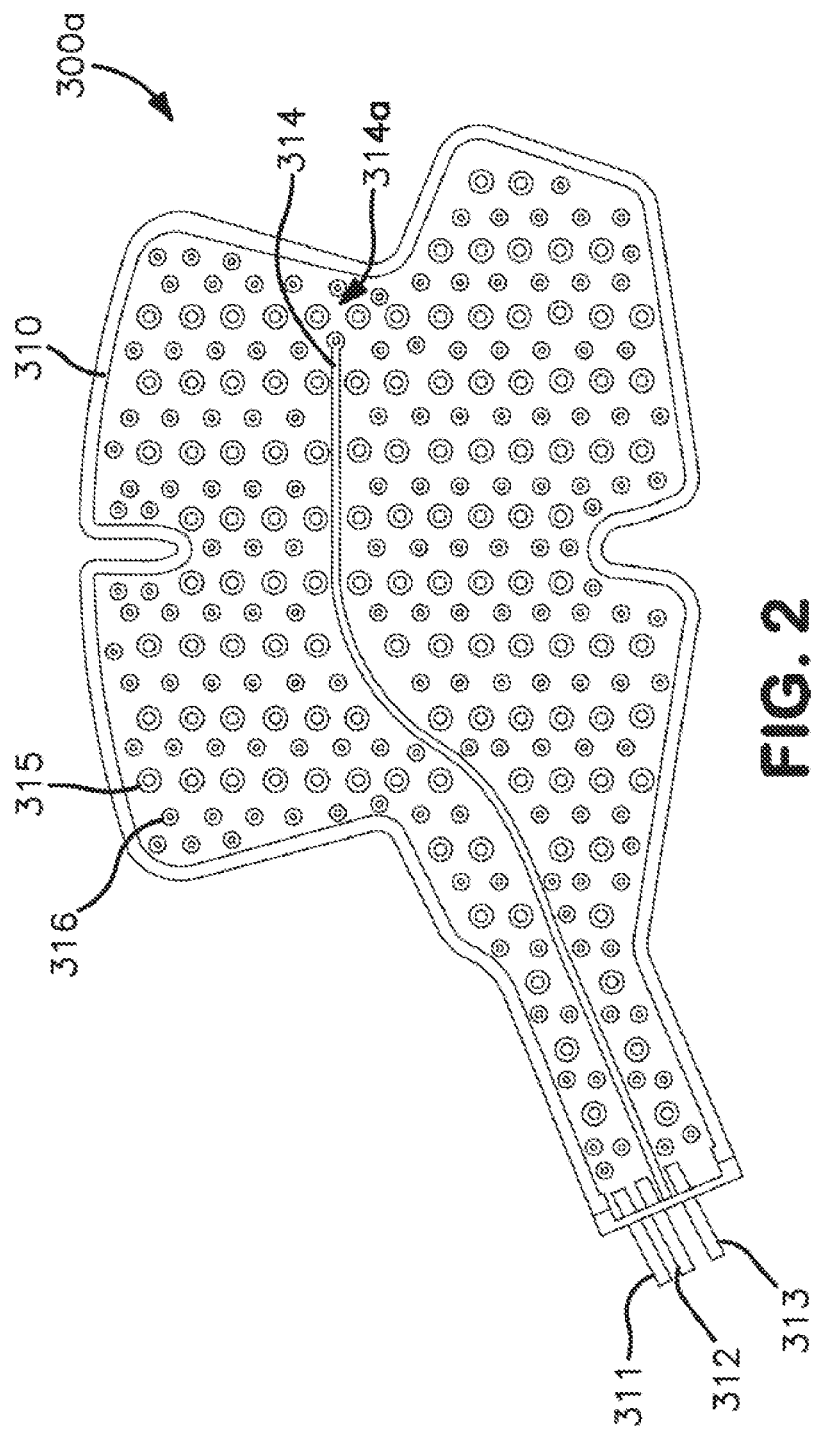
FIG. 2 is a plan view of a wrap having an elongated arm and a gradient fluid pathway.
Figure 3:
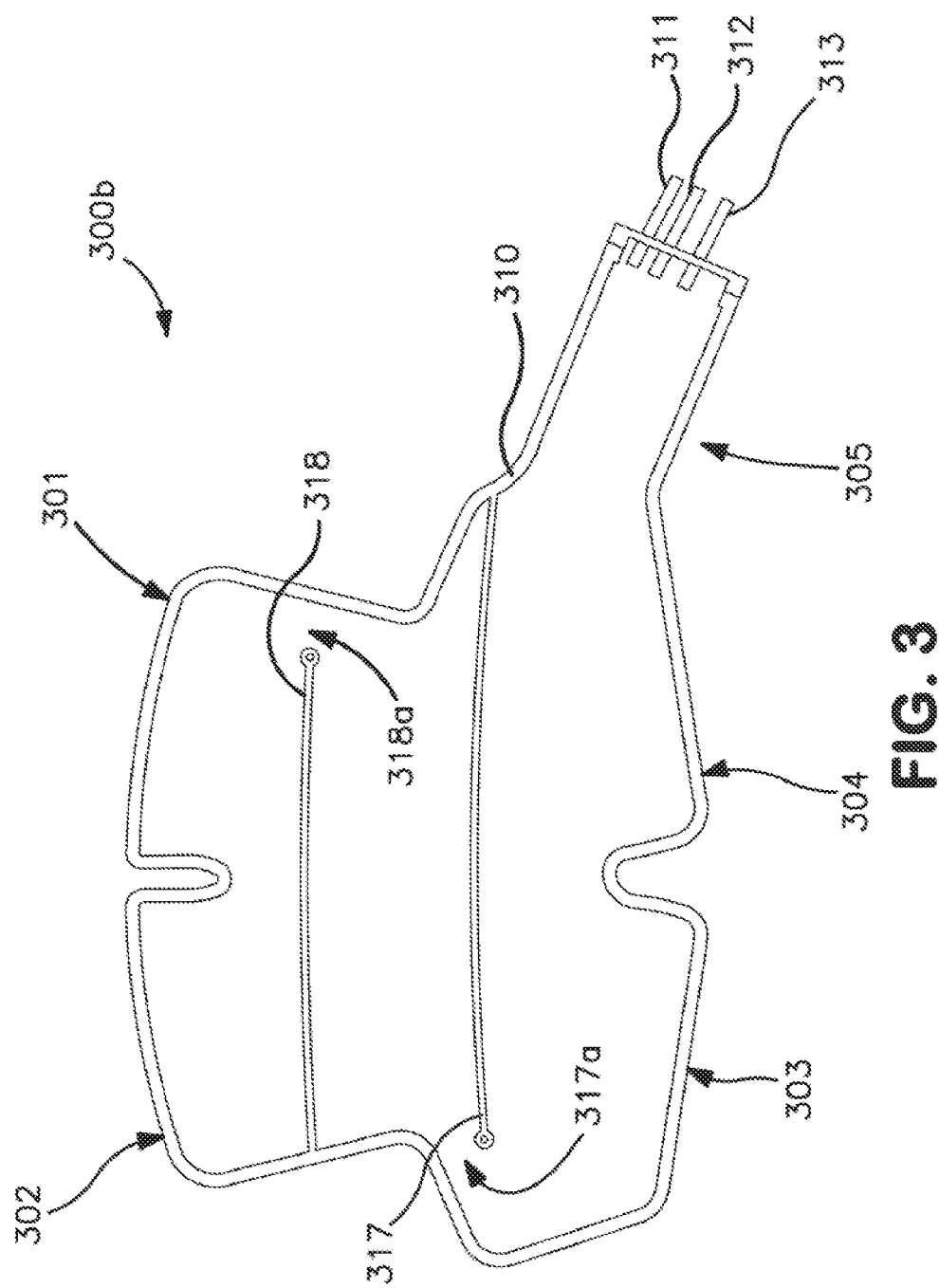
FIG. 3 is a plan view of a wrap having an elongated arm and a fluid pathway as well as a seal pattern.

Referring now to FIGS. 2 and 3, a first side of the wrap is identified as 300*a* and a second side is identified as 300*b*. The wrap in FIGS. 2 and 3 is constructed using four layers of material, all sealed together about perimeter seal 310. The wrap may be formed in two parts, which are then sealed together. In forming the first part of the wrap, a first layer of material is supplied, hoses, 311 and 313 are supplied as discussed above, and a second layer of material is supplied on top of the first layer. The first and second layers of material are sealed together about their perimeter so as to form a first cavity between them where fluid may ingress to and egress from the first cavity only by way of hoses 311 and 313. Seal 314 is also made, sealing layers one and two together and creating a fluid pathway from hose 311 around seal 314 to hose 313. While seal 314 may be of a variety of shapes, it is preferred that it simply bisects 300*a* leaving gap 314*a* between seal 314 and seal 310, where the length of gap 314*a* is preferably shorter than the length of seal 314. Additional patterned seals may also be formed, such as the pattern of comparatively large circular seals 315 and small circular seals 316 depicted in FIG. 2. The patterned seals minimize wrap deformation, keeping the overall profile of the wrap low. The patterned seals also help evenly distribute fluid throughout the entirety of the wrap.

The second part of the wrap is formed similarly. A third layer of material is supplied and a hose 312 is also supplied as described above. A fourth layer of material is supplied on top of the third layer of material and a seal 310 is created about their perimeters to as to seal the layers together and form a cavity between them where fluid may ingress to and egress from the cavity only by way of hose 312. Additionally, one or more additional seals may be created between the two sheets in order to create one or more channels in the cavity. As shown in FIG. 3, seal 317 contacts seal 310 at or near arm 305 and it extends almost the entire length of the wrap leaving gap 317*a* between seal 310 and seal 317 at the distal end of seal 317. The length of gap 317*a* is preferably shorter than the length of seal 317. Thus, fluid entering the cavity by way of hose 312 will be forced along the entire length of seal 317 before it is able to traverse the gap 317*a* and make its way up the wrap.

Additional seals may be added to further direct fluid flow. As shown in FIG. 3, seal 318 extends from seal 310 at a point above gap 317*a* along nearly the entire length of the wrap leaving gap 318*a* between seal 310 and seal 318 at the distal end of seal 318. The length of gap 318*a* is preferably shorter than the length of seal 318. That configuration of seals forces fluid to traverse the lower portion of the wrap then flow through gap 317*a*, traverse back along the wrap and flow through gap 318*a*, before traversing the length of the wrap again. In so doing, the fluid creates a pressure gradient that forces bodily fluid, such as blood, from the lower back up toward the individual's heart. The fluid in the wrap may be repeatedly drained and refilled so as to provide a pumping effect to help blood flow in an individual. Additional seals to further direct fluid flow could also be added.

It should be appreciated that the first half of the wrap, shown in FIG. 2, could be utilized on its own as a complete therapy wrap as could the second half, shown in FIG. 3. It is preferable, however, that the first and second halves are joined together by sealing the four layers of material about seal 310. So joined, the resultant wrap is constructed of four layers of material and at least two cavities, each of the two cavities having differing sealing patterns. One pattern, shown in FIG. 2, ensures that fluid supplied to a first cavity is distributed evenly throughout the wrap while the other pattern, shown in FIG. 3, ensures that the fluid supplied creates a pressure gradient.

Figure 4:
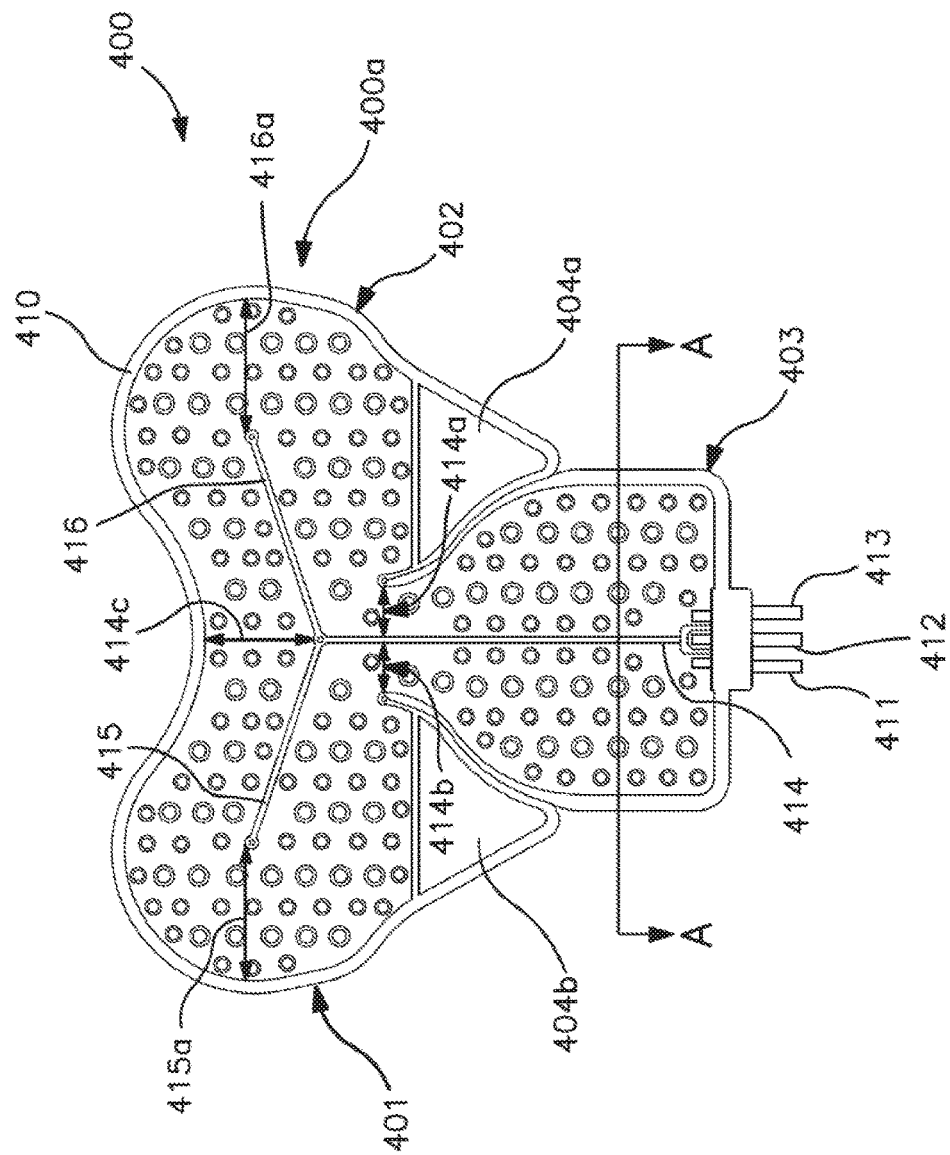
FIG. 4 is a plan view of a wrap having a shape similar to the capital letter T or Y and having a fluid pathway and seal pattern.
Figure 5:
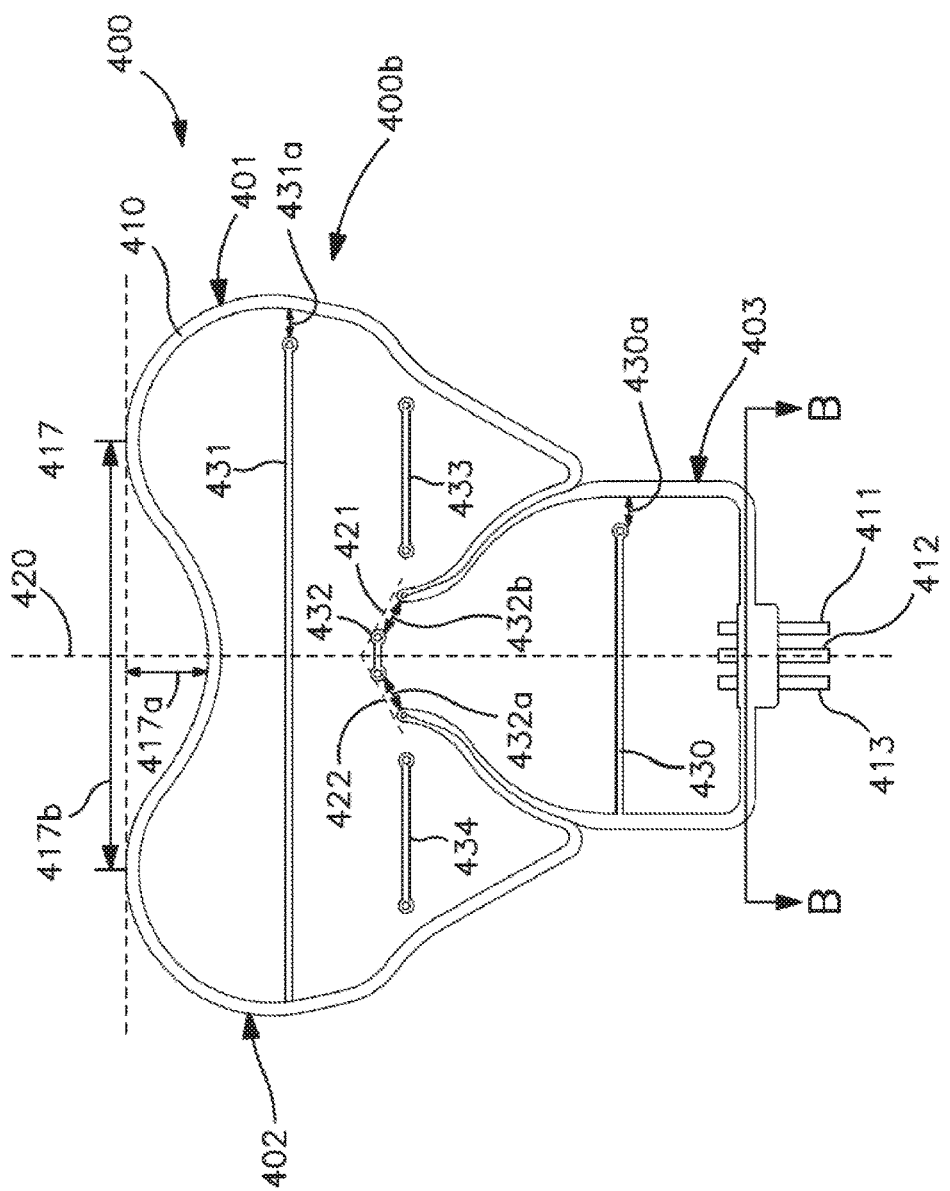
FIG. 5 is a plan view of a wrap having a shape similar to the capital letter T or Y and having a gradient fluid pathway.

Referring to FIGS. 4 and 5, and another wrap 400 is provided. It should be appreciated that the method of construction of wrap 400 may be achieved in essentially the same manner as the construction of wrap 300, particularly with respect to sealing multiple sheets and hoses together to form cavities between the sheets so as to only allow for the ingress and egress of fluid through the hoses. The shape of wrap 400 is different however. Wrap 400 includes three lobes, lobe 401, lobe 402 and lobe 403 (roughly defined in FIG. 5 by hash lines 420, 421 and 422). Thus the shape of the wrap may be viewed as essentially triangular or clover like, or in a broad sense as the shape of the capital letter Y or T where, for example, lobes 401 and 402 form the horizontal cross member of the letter T, lobe 401 forming the first half of the cross member and lobe 402 forming the second half of the cross member, while lobe 403 forms the vertical base member of the letter T, all as shown in FIG. 5. Each lobe extends generally from the center point of the wrap and terminates at a distal end which is generally the area of lobe which is furthest from the center point. Wrap 400 also includes two fastening sections, 404a and 404b. Each fastening section may include any one of a variety of fasteners such as hook and loop, buttons, snaps, eyelets that may be tied together or the like. While it is preferable that the fasteners are of a variety that releasable, that is, they may be repeatedly connected and disconnected, it is possible that the fasteners are permanent, such as sealing together fastener sections 404b and 404a using RF welding.

Depicted in FIG. 4 is side 400a, which is constructed utilizing at least two sheets of material and at least two hoses where the two sheets are sealed together about their perimeters to from a cavity and at least two hoses are provided such that fluid may ingress to and egress from the cavity only by way of the hoses. Additionally, seals 414, 415 and 416 may be formed. The seals form a fluid pathway in the cavity such that fluid entering the cavity from hose 411 is forced around the seals, through the cavity before it may egresses from hose 413. Preferably, seal 414 bisects the entirety of lobe 403 and extends partially up along the imaginary dividing line between lobes 401 and 402 leaving gap 414a between seal 414 and seal 410—roughly at the imaginary line 422 between lobe 403 and 402—leaving gap 414b between seal 414 and seal 410—roughly at the imaginary line 421 between lobe 403 and 401—and leaving gap 414c between the distal end of seal 414 and seal 410—roughly along imaginary line 420. Extending from the distal end of seal 414 are seals 415 and 416. Seal 415 extends from seal 414 into lobe 401 toward seal 410 leaving gap 415a between the distal end of seal 415 and seal 410. Seal 416 extends from seal 414 into lobe 402 toward seal 410 leaving gap 416a between the distal end of seal 416 and seal 410. Preferably, gaps 414c, 415a and 416a are shorter than the lengths of seals 414, 415 and 416 respectively. It is also preferable that seals 414, 415 and 416 form the roughly the shape of a capital letter Y. Patterned seals may also be formed in wrap 400.

FIG. 5 depicts the opposite side of wrap 400, generally identified as 400b which is preferably constructed utilizing at least two sheets of material and at least one hose where the two sheets are sealed together about their perimeters to from a cavity and the hose is provided such that fluid may ingress to and egress from the cavity only by way of the hose. Additional seals may be made in the material forming the cavity. For example, seal 430 extends from seal 410 across lobe 403 such that a gap 430a is formed between the distal end of seal 430 and seal 410. Seal 431 is formed so as to extend from seal 410 and traverse across lobes 401 and 402 such that a gap 431a is formed between the distal end of seal 431 and seal 410. Other seals, such as seal 432 may be formed approximately at the junction point between lobe 403 and lobes 401 and 402. Seal 432 is preferably formed between seal 410, creating gap 432a and gap 432b. Seals 433, formed in lower portion lobe 401, and seal 434, formed in the lower portion of lobe 402 may also be provided. Seals 430 and 431 assist in forming a pressure gradient as fluid flows into the cavity through hose 412. The additional seals 432, 433 and 434 also assist in creating a pressure gradient in addition to preventing the wrap 400 from deforming and ballooning up. When fluid is introduced into the cavity, seals 432 through 434 prevent the layers of material forming the cavity from expanding too far away from one another and thereby maintain a thinner profile in wrap 400 than would otherwise exist without the seals when the cavity was filled with fluid.

As mentioned previously, the preferable shape of wrap 400 approximates a clover, or a capital letter Y. While wrap 400 could approximate the capital letter T, the Y shape provides an indentation, or valley 417 identified in FIG. 5, between the uppermost portions of lobes 401 and 402. As shown in FIG. 5, the depth of the valley is identified as 417a and the span of the valley is identified as 417b. Preferably, the span 417b is grater than the depth 417a. The presence of the valley is preferable in that allows for the wrap to be positioned on an individual's shoulder while accommodating the sloping junction point between the individual's trapezius and levator scapulae muscles in the upper back and neck and the deltoid musculature in the shoulder. Primarily the trapezius muscles tend to slope downward from an individual's neck toward the deltoid, and the valley 417 helps minimize the wrap's contact with the slope of the trapezius. Minimizing that contact allows the wrap 400 to remain seated on the shoulder of the individual and not be lifted up or pulled away from the shoulder by the trapezius and allow for lobes 401 and 402 extend into the individual's back and chest and maximize their contact with those areas.

The unique shape of wrap 400 facilitates its manipulation into the formation of a cup which can then, preferably, be applied over an individual's shoulder. In practical application, considering FIG. 4, lobe 403 is lifted up and lobes 402 and 403 are slid underneath lobe 403 bringing fastener sections 404a and 404b together. Wrap 400 may then be inverted such that, side 400b forms the exterior of the cup while side 400a forms the interior of the cup. In such a configuration, wrap fastening sections 404a and 404b may be fastened together in order to maintain the cup shape. Once joined, lobes 401 and 402 will help maintain the position of lob 403 against the individual's body when the wrap is applied.

The cup shape of wrap 400 is particularly suitable for applying therapy to an individual's shoulder. With fastening sections 404a and 404b fastened, the wrap may be placed over, for example, an individual's right shoulder. Preferably, wrap 400 is further secured to the individual's shoulder by way of a harness or strap that connects to wrap 400, using hook and loop fasteners for example, and surrounds the individual's torso. Fluid may then be allowed to ingress to and egress from the wrap through hoses 411, 412 and 413. Fastening sections 404a and 404b keep lobe 403 against the individual's shoulder and arm in order to ensure that therapy is applied to that area of the body. The cup formation ensures that lobes 401 and 402 each maintain contact with shoulder area as well, one lobe essentially contacting the pectoralis major and the frontal area of the deltoid while the other lobe essentially contacts the lower trapezius and rear area of the deltoid. Thus, the cup shape of wrap 400 ensures that the wrap maintains contact with the body even when filled with fluid and does not deform and balloon away from the area of the body requiring therapy.

Figure 6:
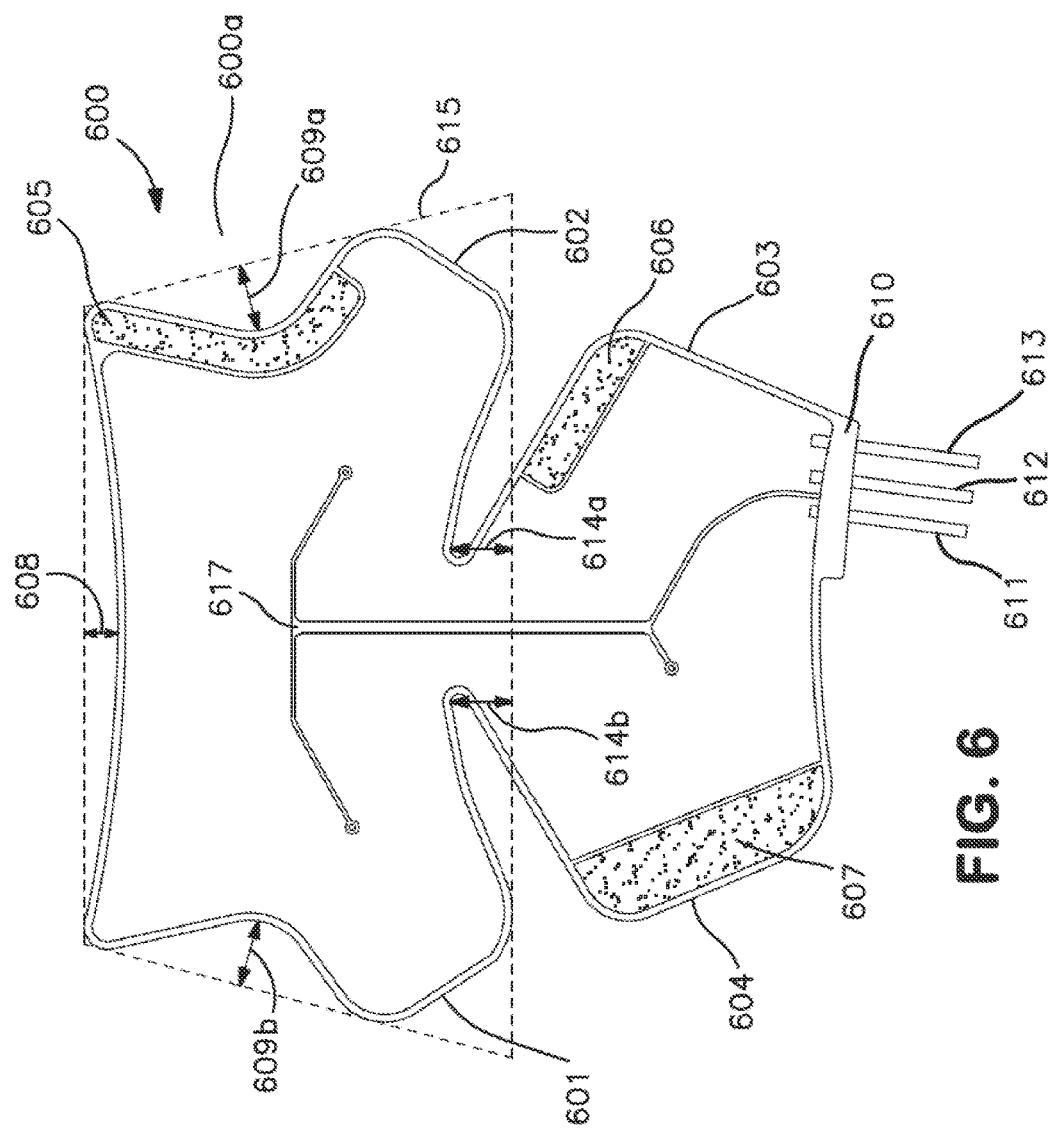
FIG. 6 is a plain view of a wrap having a shape similar to that of a trapezoid connected to a pentagon and a fluid pathway.
Figure 7:
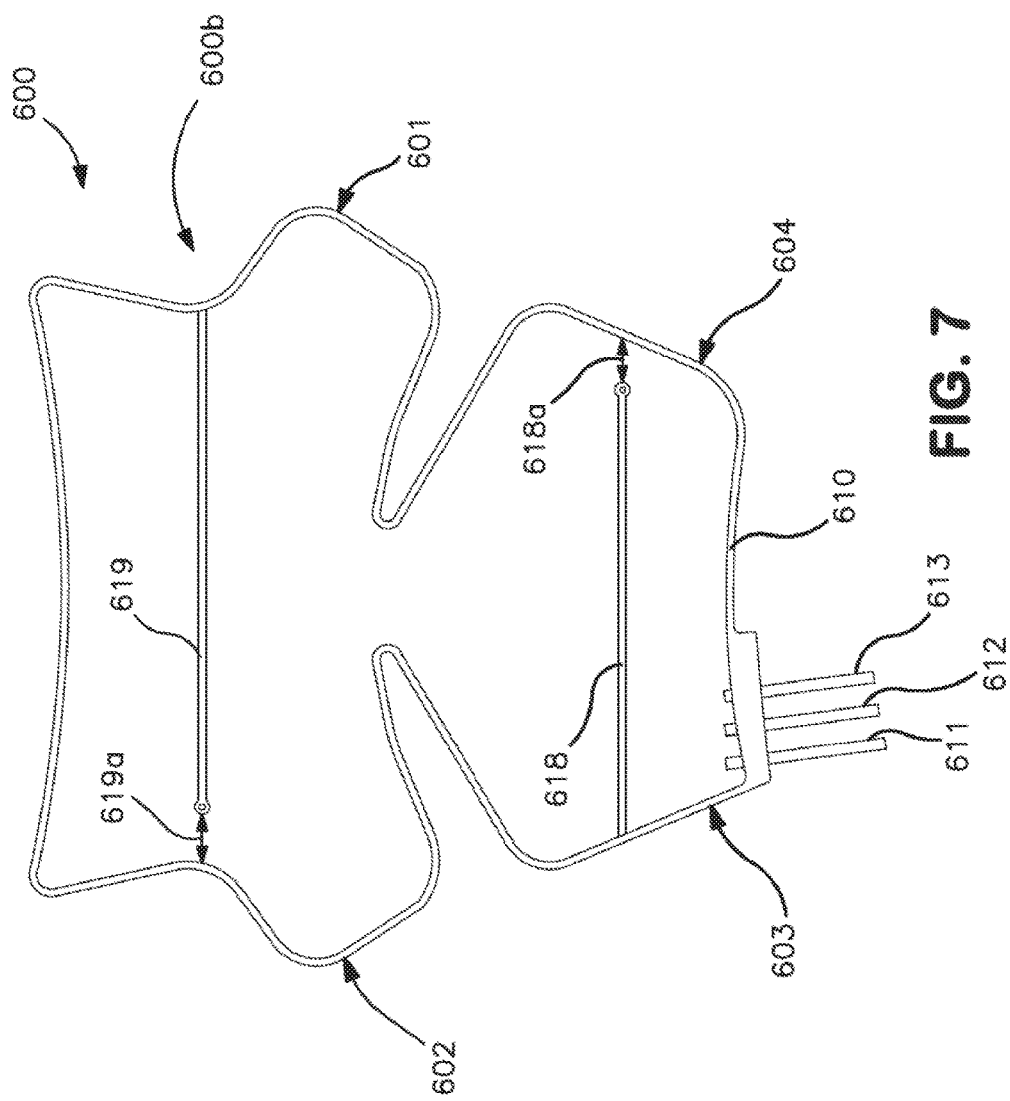
FIG. 7 is a plan view of a wrap having a shape similar to that of a trapezoid connected to a pentagon and having a gradient fluid pathway.

Another wrap is wrap 600 depicted in FIGS. 6 and 7. FIG. 6 shows a first side 600a of wrap 600 and FIG. 7 shows a second side 600b of wrap 600. Wrap 600 is designed to surround an individual's foot, ankle and lower calf. The basic construction of wrap 600 is similar to the other wraps discussed herein in that four sheets of material are sealed together to create at least two chambers and three hoses are also provided to allow for fluid to ingress to and egress from the chambers. However, wrap 600 differs in shape than the previously discussed wraps. As shown in FIG. 6, wrap 600 includes four lobes, 601, 602, 603, and 604. The overall shape wrap, defined by perimeter seal 610, is essentially symmetrical when bisected along a longitudinal axis. That is, lobe 601 mirrors lobe 602 and lobe 603 mirrors lobe 604.

The basic shape of wrap 600 is that of a trapezoid joined to a pentagon. The trapezoid may be said to have a top and a base, where the length of the top is less than the length of the base, and the sides form acute angles as they extend away from the base toward the top while also forming obtuse angles as they extend away from the top toward the base. The pentagon may be said to be formed of a triangle and a trapezoid, where one side of the triangle forms the base of the trapezoid, and the point of the triangle, opposite that base, constitutes the top of the pentagon.

The two upper lobes, 601 and 602, generally form a trapezoid (roughly outlined by hash line 615), each lobe 601 and 602 forming half of the trapezoidal shape, while the two lower lobes, 603 and 604, generally form a pentagon, each lobe 603 and 604 forming half of the pentagonal shape. All of the lobes meet approximately in the middle of the base trapezoid formed by lobes 601 and 602, and at the top point of the pentagon formed by lobes 603 and 604 thereby forming a cavity bounded by seal 610.

In the preferred embodiment, as can be seen in FIG. 6, the perimeters of lobes 601 and 602 vary from the traditional trapezoidal shape 615. The base of each of lobes 601 and 602 are angled upward from the base of the trapezoid such that gaps 614a and 614b are created. The side of each of lobe 601 and 602 are also indented so as to form a wide U, V or L shape, the distance between the well of each indention and the sides of trapezoid 615 being 609b and 609a, respectively. The tops of lobes 601 and 602 also curve down towards a middle point where they are joined together such that the top of the wrap exhibits a slight curve over the majority, if not the entirety, of its length. The curvature of the top of lobes 601 and 602 creates a gap 608 between the tops of the lobes and trapezoid 615.

The shape of wrap 600 is designed to allow the wrap to conform to the unique shape of an individual's foot, ankle and lower calf. In practice, an individual aligns his foot such that the individual's heal is placed in the upper trapezoidal portion, the individual's arch bridges the connection point between the upper and lower portions, and the individual's toes are located in the pentagonal section, oriented closest to hoses 611, 612, and 613. To secure the wrap 600, lobe 601 is lifted up then wrapped around the individual's ankle. Lobe 602 is lifted up and wrapped over lobe 601, also around the individual's ankle. Fastener segment 605, which includes a fastener such as hooks, is then secured to the exterior of lobe 601. Thus the upper portions of lobes 601 and 602 surround the individual's ankle and lower calf.

The gaps 609a and 609b follow the shape of the individual's ankle and foot. Without the gaps 609a and 609b, the wrap would crease at the front of the individual's ankle, where the leg meets the top of the individual's foot, thereby inhibiting or cutting off the flow of fluid into portions of lobes 601 and 602. Additionally, the curvature of the top of lobes 601 and 602, resulting in gap 608, allows the wrap to fit snuggly against the conical shape of the individual's calf and ankle. Without the gap 608, the lobes 601 and 602 would tend to form a cylindrical shape instead of a cone and thus the wrap would fit tightly on the individual's lower calf but would be loose at the individual's ankle, or lobes 601 and 602 would have a tendency to kink and block fluid flow, in either case resulting in inadequate therapy being applied to the ankle and calf areas.

With lobes 601 and 602 secured, lobe 603 is folded over the top of the individual's foot and toes and fastener section 606, which includes a fastener such as hooks, is secured to the exterior of lobe 602. Lobe 604 is then folded over the top of the individual's foot and toes, and over lobe 603, and fastening section 607, which likewise includes a fastener such as hooks, is secured to the exterior of lobe 603. With wrap 600 so secured, fluid may be introduced to the cavities of the wrap by way of hoses 611, 612 and 613. Preferably, where wrap 600 is constructed of four sheets of material having at least two cavities formed between them, hoses 611 and 613 communicate with the cavity closest to the individual's skin, referred to as the interior cavity, while hose 612 communicates with another cavity, such as the most exterior cavity. It should be appreciated that the exterior of wrap 600, generally referenced as 600b in FIG. 7, is preferably constructed using a material havening sufficient nap such that the hooks of a hook and loop fastening system are able to engage the nap as they would normally engage loops. Alternately, loop sections could be affixed to side 600b such that the fastening sections 605, 606 and 607 would engage the loops when the wrap is properly applied to an individuals foot, or a different fastening system, such as buttons or snaps could be implemented in place of the hook and loop system.

Additional seal 617 may be provided so as to create a channel in the interior cavity. When fluid is pumped into the interior cavity through hose 611, the channel created by seal 617 forces the fluid along one half of the individual's foot, moving from the toes toward the heel. Thereafter the fluid progresses around the ankle bone and up the ankle to the lower calf where it circles around the back of the individual's calf before descending down the opposite side of the individual's ankle and around the opposite ankle bone. The fluid then progresses down to the individual's heel and back along the opposite side of the individual's foot toward the toes where it is expelled through hose 613. As with the other wraps discussed herein, it is further contemplated that the cavity having seal 617 could have additional seals, such as pattern seals formed within it (not shown).

Where wrap 600 is formed of at least four sheets of material, another chamber, the exterior chamber for example, may also include additional seals. FIG. 7 is a depiction of the exterior side of wrap 600, identified as 600b. As shown in FIG. 7, seal 618 is created between at least two sheets defining a cavity. Seal 618 extends from the perimeter of lobe 603 across the width of wrap 600 and nearly to seal 610 which, in FIG. 7 is the seal defining the perimeter of the cavity, leaving gap 618a between the distal end of seal 618 and seal 610. It should be apparent that additional seals could be added that would alter the perimeter of the cavity, but for explanatory purposes, the seal 610 will be identified as the perimeter of the cavity. Additionally, a seal 619 is made in the cavity extending from the perimeter of the cavity in lobe 601 across the width of wrap 600 nearly to seal 610 of the cavity, leaving gap 619a. Consequently, when fluid is pumped into the external cavity through hose 612, the fluid is forced along seal 618, through gap 618a, up through the wrap into lobes 601 and 602, then through gap 619a and back across the wrap moving from lobe 602 into lobe 601 across the top of seal 619. In practical application, when an individual has secured the wrap to his foot, ankle and lower calf as explained above, the movement of fluid as just described creates a pressure gradient in the individual's foot beginning at the toes, moving along the foot to the heel and ankle, then increasing pressure up the ankle and finally up into the calf. The creation of such a pressure forces fluid in the body, such as blood, from the toes and foot back up into the leg and toward the heart.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A therapy wrap comprising:
   a first layer of material, a second layer of material, a third layer of material, a fourth layer of material, a first hose, and a second hose, wherein each of said first hose and said second hose includes a first end, a second end an exterior perimeter, and an interior pathway;
   wherein said first layer of material and said second layer of material are sealed together along a first cavity seal such that a first cavity is formed between said first layer of material and said second layer of material, the first cavity seal defining a shape of the first cavity;
   wherein said third layer of material and said fourth layer of material are sealed together along a second cavity seal such that a second cavity is formed between said third layer of material and said fourth layer of material, the second cavity seal defining the shape of the second cavity;
   wherein said first hose provides an access pathway to said second cavity;
   wherein the therapy wrap includes a top section and a bottom section, said top section having a trapezoidal shape having a top, a base, and sides and said bottom section having a pentagonal shape;
   wherein said top section is joined with bottom section such that the bottom section overlaps the base of the trapezoidal top section in a middle third of the length of the base of the trapezoidal top section at a junction;
   wherein the first hose traverses a section of the second cavity seal defining a side of the pentagonal shape of the bottom section of the therapy wrap;
   a first pathway seal having a proximal end and a distal end and a second pathway seal having a proximal end and a distal end, wherein the first pathway seal and second pathway seal each seal together the first layer and the second layer, and wherein said proximal end of said first pathway seal is connected to said first cavity seal at a point along a portion of said first cavity seal that defines a first side of said top section;
   wherein said proximal end of said second pathway seal is connected to said first cavity seal at a point along a portion of said first cavity seal that defines a second side of said bottom section;
   wherein said first pathway seal extends across said first cavity and terminates at said distal end of said first pathway seal such that a top section gap exists between said distal end of said first pathway seal and a second side of said top section;
   wherein said second pathway seal extends across said first cavity and terminates at said distal end of said second pathway seal such that a bottom section gap exists between said distal end of said second pathway seal and a first side of said bottom section wherein the bottom section is joined to the top section at said junction formed between a point of the pentagonal shape of the bottom section and the base of the trapezoidal shape of the top section;
   a back side pathway seal;
   wherein the first hose and said second hose are provided along the side of the pentagonal shape opposite the point joining the bottom section to the top section;
   wherein said back side pathway seal seals together said third layer of material and said fourth layer of material and extends from the second cavity seal at a point between said first hose and said second hose and extends through the bottom section and into the top section towards the top of the trapezoidal shape of the top section.

2. The therapy wrap of claim 1 wherein the second hose traverses a section of the second cavity seal defining a side of the pentagonal shape opposite the junction joining the bottom section to the top section.

3. The therapy wrap of claim 2
   wherein said back side pathway seal further includes a first branch and a second branch, said first branch extending from said first back side pathway seal in said top section toward a first side of the trapezoidal top section and said second branch extends from said back side pathway seal in said top section toward a second side of the trapezoidal top section such that fluid flowing into said second cavity through the first hose and out of said second cavity through said second hose must first traverse along said back side pathway seal through a first half of the pentagonal bottom section, pass through the junction connecting said bottom section to said top section, traverse along the first branch of said back side pathway seal and around a distal end of said first branch, traverse across the top of said top section and around a distal end of said second branch, traverse back through the junction connecting said bottom section to said top section and into a second half of said pentagonal bottom section before exiting said second cavity through said second hose.

4. A therapy wrap as in claim 3 further comprising a plurality of discrete seals comprising a plurality of large seals having a first outer perimeter length and a plurality of small seals having a second outer perimeter length such that said first outer perimeter length is different from said second outer perimeter length, and wherein the plurality of discrete seals are configured to seal the third layer to the fourth layer within the second cavity;
   wherein said large seals and said small seals are arranged in a pattern that comprises a first column of two or more of said large seals, a column of two or more of said small seals, and a second column of two or more of said large seals wherein said first column of large seals is separated from said second column of large seals by said column of small seals and wherein center points of said large seals are vertically offset from center points of said small seals.

5. A therapy wrap as in claim 2 wherein said section of said second cavity seal defining a side of the pentagonal shape opposite said junction includes a first third, a second third, and a middle third of said section, wherein said middle third is between said first third and said second third; and
    wherein said first hose traverses either said first third or said second third of said section of said second cavity seal.

6. A therapy wrap as in claim 1 wherein said first pathway seal and said second pathway seal extend across said first cavity in opposite directions.

7. A therapy wrap as in claim 6 wherein said first pathway seal and said second pathway seal are substantially parallel to each other.

8. A therapy wrap comprising a first layer of material, a second layer of material, a third layer of material, a fourth layer of material, a first hose, a second hose, and a third hose, each hose including a first end, a second end, an exterior perimeter, and an interior pathway;
    wherein the first layer of material is a front side of said therapy wrap and the fourth layer of material is a back side of said therapy wrap;
    wherein the first layer of material and the second layer of material are sealed together along a first cavity seal such that a first cavity is formed between the first layer and the second layer, the first cavity seal defining a shape of the first cavity;
    wherein the third layer of material and the fourth layer of material are sealed together along a second cavity seal such that a second cavity is formed between the third layer and the fourth layer, the second cavity seal defining a shape of the second cavity;
    wherein the first cavity seal and the second cavity seal have substantially the same shape and said first cavity seal and said second cavity seal are sealed together such that said first cavity seal and said second cavity seal are a single continuous seal that joins said first layer, said second layer, said third layer, and said fourth layer together and defines a shape of the therapy wrap;
    wherein said first hose is provided such that the first end of said first hose is exterior to the first cavity and the second end of said first hose is interior to the first cavity, said second hose is provided such that the first end of said second hose is exterior to the second cavity and the second end of said second hose is interior to the second cavity, said third hose is provided such that the first end of said third hose is exterior to the second cavity and the second end of said third hose is interior to the second cavity;
    wherein said first cavity seal is formed around the exterior perimeter of said first hose, said second cavity seal is formed around the exterior perimeter of said second hose and said second cavity seal is formed around the exterior perimeter of said third hose;
    wherein the shape of the therapy wrap includes a top section and a bottom section, said top section having a trapezoidal shape having a top, a base, and sides and said bottom section having a pentagonal shape;
    wherein said top section is joined with bottom section such that the bottom section overlaps the base of the trapezoidal top section in a middle third of the length of the base of the trapezoidal top section at a junction; and
    wherein said first hose, said second hose, and said third hose cross a section of the continuous seal defining a side of the pentagonal shape of the bottom section;
    a first pathway seal having a proximal end and a distal end and a second pathway seal having a proximal end and a distal end wherein said proximal end of said first pathway seal is connected to said first cavity seal at a point along a portion of said first cavity seal that defines a first side of said top section;
    wherein said first pathway seal and said second pathway seal are formed on the front side of said therapy wrap and not on said back side of said therapy wrap;
    wherein said proximal end of said second pathway seal is connected to said first cavity seal at a point along a portion of said first cavity seal that defines a second side of said bottom section;
    wherein said first pathway seal extends across said first cavity and terminates at said distal end of said first pathway seal such that a top section gap exists between said distal end of said first pathway seal and a second side of said top section;
    wherein said second pathway seal extends across said first cavity and terminates at said distal end of said second pathway seal such that a bottom section gap exists between said distal end of said second pathway seal and a first side of said bottom section
    wherein said first pathway seal and said second pathway seal divide said first cavity into an S shape such that fluid entering said first cavity must flow along the length of said first pathway seal before passing around said distal end of said first pathway seal and flowing along a bottom side of said second pathway seal before passing said distal end of said second pathway seal and flowing along a top side of said second pathway seal;
    said therapy wrap further comprising a back side pathway formed on said back side and not on said front side;
    wherein said back side pathway seal extends from said second cavity seal at a point between said second hose and said third hose and extends through the bottom section and into the top section toward the top of the trapezoidal shape of the top section; and
    wherein said back side pathway seal further includes a first branch and a second branch, said first branch extending from said back side pathway seal in said top section toward a first side of the trapezoidal top section and said second branch extends from said back side pathway seal in said top section toward a second side of the trapezoidal top section such that fluid flowing into said second cavity through the second hose and out of said second cavity through said third hose must first traverse along said back side pathway seal through a first half of the pentagonal bottom section, pass through the junction connecting said bottom section to said top section, traverse along the first branch of said pathway seal and around a distal end of said first branch, traverse across the top of said top section and around a distal end of said second branch, traverse back through the junction connecting said bottom section to said top section and into a second half of said pentagonal bottom section before exiting said second cavity through said third hose.

9. The therapy wrap of claim 8 wherein said junction is formed between said top section and said bottom section such that the bottom section is joined to the top section at a point of the pentagonal shape of the bottom section and the base of the trapezoidal shape of the top section, and wherein the first hose crosses a section of the continuous seal defining a side of the pentagonal shape opposite the junction joining the bottom section to the top section.

10. The therapy wrap of claim 8 wherein said first hose, said second hose, and said third hose each cross a section of the single continuous seal defining a side of the pentagonal shape opposite the junction joining the bottom section to the top section.

11. A therapy wrap as in claim 8 further comprising a plurality of discrete seals formed on said back side of said therapy wrap and not on said front side of said therapy wrap, said plurality of discrete seals comprising a plurality of large seals having a first outer perimeter length and a plurality of small seals having a second outer perimeter length such that said first outer perimeter length is different from said second outer perimeter length and wherein the plurality of discrete seals are configured to seal the third layer to the fourth layer within the second cavity;
  wherein said large seals and said small seals are arranged in a pattern that comprises a first column of two or more of said large seals, a column of two or more of said small seals, and a second column of two or more of said large seals wherein said first column of said large seals is separated from said second column of said large seals by said column of said small seals and wherein center points of said large seals are vertically offset from center points of said small seals.

* * * * *

UNITED STATES PATENT AND TRADEMARK OFFICE
CERTIFICATE OF CORRECTION

| | |
|---|---|
| PATENT NO. | : 9,931,240 B2 |
| APPLICATION NO. | : 14/730470 |
| DATED | : April 3, 2018 |
| INVENTOR(S) | : Michael L. Wilford and David Slack |

Page 1 of 1

It is certified that error appears in the above-identified patent and that said Letters Patent is hereby corrected as shown below:

In the Specification

Column 2, Line 1, delete "together to from" and insert --together to form--;
Column 3, Line 1, delete "manipulates so as to" and insert --manipulated so as to--;
Column 4, Line 43, delete "embodiment of the" and insert --embodiment as--;
Column 4, Line 47, delete "are place on top" and insert --are placed on top--;
Column 6, Line 18, delete "1 trough 7." and insert --1 through 7.--;
Column 6, Line 32, delete "to so that the wrap" and insert --so that the wrap--;
Column 6, Line 43, delete "uniform sheets" and insert --uniform same sheet--;
Column 8, Line 24, delete "perimeters to as to" and insert --perimeters as to--;
Column 9, Line 22, delete "variety that releasable" and insert --variety that are releasable--;
Column 9, Line 34, delete "egresses from hose" and insert --egress from hose--;
Column 9, Line 58, delete "form the roughly the shape" and insert --form roughly the shape--;
Column 10, Line 49, delete "position of lob" and insert --position of lobe--;
Column 11, Line 43, delete "between the well" and insert --between the wall--;

In the Claims

Claim 4, Column 14, Line 61, delete "large seals wherein" and insert --large first type seals wherein--;
Claim 4, Column 14, Line 61, delete "large seals is" and insert --large first type seals is--;
Claim 4, Column 14, Line 62, delete "large seals" and insert --large first type seals--;
Claim 4, Column 14, Line 64, delete "large seals" and insert --large first type seals--.

Signed and Sealed this
Seventh Day of August, 2018

Andrei Iancu
*Director of the United States Patent and Trademark Office*